United States Patent [19]

Coquelet et al.

[11] Patent Number: 4,929,635

[45] Date of Patent: May 29, 1990

[54] NEW DERIVATIVES OF 4-VINYL BENZOIC ACID, PROCESS FOR THEIR PREPARATION AND THEIR USES IN THERAPEUTICS AND AS LIGANDS

[75] Inventors: Claude Coquelet, St Gely-du-Fesc; Samia Roussillon, Gignac; Daniel Sincholle, St-Clement-la-Riviere; Claude Bonne, Bry-sur-Marne; Alain Alazet, Agde, all of France

[73] Assignee: Laboratoires Chauvin-Blache, Montpellier, France

[21] Appl. No.: 817,839

[22] PCT Filed: Apr. 3, 1985

[86] PCT No.: PCT/FR85/00074

§ 371 Date: Dec. 5, 1985

§ 102(e) Date: Dec. 5, 1985

[87] PCT Pub. No.: WO85/04652

PCT Pub. Date: Oct. 24, 1985

[30] Foreign Application Priority Data

Apr. 6, 1984 [FR] France .................. 84 05531

[51] Int. Cl.[5] .................. A61K 31/38; C07D 333/22

[52] U.S. Cl. .................. 514/438; 514/237.5; 514/252; 514/255; 514/256; 514/544; 514/568; 514/617; 514/231.5; 549/77; 549/79; 544/146; 544/176; 544/379; 544/391; 560/8; 562/405; 564/161

[58] Field of Search .................. 549/79, 77; 564/161; 562/495, 405; 514/230, 252, 255, 256, 438, 544, 568, 617; 544/146, 178, 379, 391; 560/8

[56] References Cited

U.S. PATENT DOCUMENTS

Re. 27,031 1/1971 Okubo .
4,723,028 2/1988 Shudo .................. 562/495

FOREIGN PATENT DOCUMENTS 0084667 8/1983 European Pat. Off. .
2422620 12/1978 France .

Primary Examiner—Alan Siegel
Attorney, Agent, or Firm—Wegner & Bretschneider

[57] ABSTRACT

The invention relates to compounds of the formula

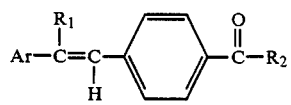

These compounds may be used in therapeutics for the treatment of acne, psoriasis, disorders of keratinization, in certain forms of cancer and as healing agents, particularly in the ocular field.

14 Claims, No Drawings

NEW DERIVATIVES OF 4-VINYL BENZOIC ACID, PROCESS FOR THEIR PREPARATION AND THEIR USES IN THERAPEUTICS AND AS LIGANDS

The present invention relates to new derivatives of 4-vinyl benzoic acid which have an activity on growth and the differentiation of biological tissues and which may be used in therapeutics for the treatment of acne, psoriasis, disorders of keratinization, in certain forms of cancer and as healing agents, particularly in the ocular field.

Vitamin A is essential for certain functions such as vision, growth and reproduction. It plays an important part in the control of growth and of the differentiation of epithelial tissues. Vitamin A deficiency causes a cutaneous hyperkeratosis and a keratinizing metaplasia of the mucous membranes.

Although the mode of action of the retinoids (analogs of Vitamin A) is still poorly understood, it has been shown:

that they slow down growth and the development of precancerous and cancerous cells;

that they possess an anti-inflammatory effect and can take part in the mechanism of healing by acting at the level of protein synthesis indispensable to the process of tissure repair.

The retinoids are used as therapeutic agents for the treatment of acute acne and psoriasis, as well as disorders of keratinization. However, although very effective, these products have the major drawback of showing side effects which are not negligible: hypervitaminosis-A, toxicity, irritation.

In FR-A-2 422 620, derivatives of stilbene are described showing certain analogy in structure and activity with the retinoids.

The object of the present invention is to provide new compounds which link with the receptor of retinoic acid (C.R.A.B.P.) at the tissue level and show a therapeutic interest similar to the retinoids without having the toxic effects thereof, particularly in the ocular field.

Thus the present invention relates to compounds of the formula (I)

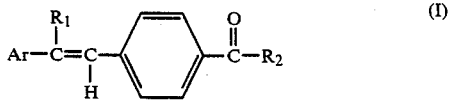
(I)

in which:

$R_1$ represents a methyl group;

Ar represents a phenyl group, a phenyl group substituted by a $C_1-C_4$ alkyl group, a 5-11 membered monocyclic heteroaromatic group containing one or two heteroatoms selected from nitrogen, oxygen and sulfur, of such a heteroaromatic group substituted by a $C_1-C_4$ alkyl group;

$R_2$ represents a hydroxy group; an amino group of the formula

in which $R_3$ and $R_4$ represent, independently from one another, a hydrogen atom, a $C_1-C_6$ alkyl group or amino ($C_1-C_6$ alkyl) or $R_3$ and $R_4$ form, with the nitrogen atom to which they are attached, a 5–8 membered heterocyclic group, saturated or not, and which can contain another heteroatom selected from nitrogen, oxygen and sulfur; a $C_1-C_4$ alkoxy group; a group of formula —O—Ar, Ar having the above-given meanings; an aminoalkoxy group of the formula

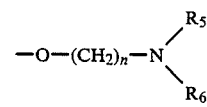

in which $R_5$ and $R_6$ represent, independently from one another, a $C_1-C_4$ alkyl group and $n=1$ to 4; and their pharmaceutically acceptable salts.

The present invention relates also to therapeutic compositions containing, as active ingredient, a compound of formula (I) or one of its pharmaceutically acceptable salts.

By the term "pharmaceutically acceptable salts", are meant the addition salts which are formed by the compounds of formula (I) having a basic group with pharmaceutically acceptable acids, as well as the salts which are formed by the compounds of formula (I) having an acid group with pharmaceutically acceptable bases.

"Addition salts with pharmaceutically acceptable acids" means the salts which give the biological properties of free bases, without having an undesirable effect. These salts may be particularly those formed with inorganic acids, such as hydrochloric acid, hydrobromic acid, sulfuric acid, nitric acid, phosphoric acid; acid metallic salts, such as disodium orthophosphate, and monopotassium sulfate, and organic acids, such as formic acid, acetic acid, propionic acid, glycolic acid, oxalic acid, fumaric acid, lactic acid, succinic acid, tartaric acid and pamoic acid.

In the same way, "salts with pharmaceutically acceptable bases" means salts which do not modify the biological properties of the free acids. These salts may be particularly those formed withh inorganic bases, such as sodium hydroxide, potassium hydroxide, lithium hydroxide, calcium hydroxide, magnesium hydroxide, or organic bases such as glucamine, N-methylglucamine, N,N-dimethylglucamine, ethanolamine, diethanolamine, morpholine, N-methyl morpholine and tris-(hydroxy-methyl)-methylamine.

A preferred class of compounds of formula (I) is that formed by the compounds having an E configuration of the molecules with respect to the double bond and more particularly the compounds of formula (I), in which $R_1$ is a hydrogen atom or a methyl group.

The compounds of formula (I) may be prepared, generally, by the Wittig reaction of a compound of formula (II)

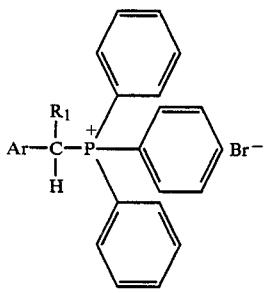

with a benzaldehyde of formula (III)

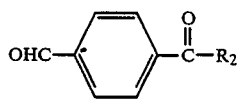

Ar, $R_1$ and $R_2$ having the previously given meaning.

This reaction generally results in isomers of E configuration.

The Z isomers may be obtained particularly by irradiation of the E isomers by U.V. radiation.

The phosphonium salts of formula (II) are obtained by a known process from corresponding aldehydes and ketones of formula

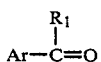

To prepare the compound of formula (I), the preferred technique is to obtain, by the process described above, the compound of formula (I) in which $R_2$ represents an ethoxy group, then, by hydrolysis, to synthesize the corresponding acid ($R_2$=OH); the corresponding esters and amides ($R_2$=alkoxy, —OA$r$,

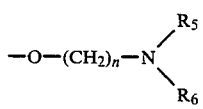

and $R_2$=

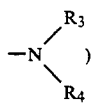

are obtained by processes currently known to the man skilled in the art from the acid by means of the acid chloride ($R_2$=Cl).

The salts of the compounds of formula (I) may be prepared conventionally by reaction with a base or an acid, in a usual solvent.

There are given below in Table I examples of compounds of formula (I) of E configuration.

The following examples illustrate the preparation of these compounds.

EXAMPLE 1

Preparation of (E) ethyl 4-[2-(4-isopropyl phenyl) propenyl]benzoate (a) Preparation of 1-(4-isopropyl phenyl) ethyltriphenyl phosphonium bromide To 0.32 mole of p.acetylcumene dissolved in 500 ml of methanol, are added at 0° C. 0.17 mole of NaBH$_4$.

It is stirred for 1 hour after the addition and the reaction mixture is poured into 2 liters of iced 1N HCl. It is extracted with diethyl ether, the organic phase is washed with a saturated solution of NaHCO$_3$, it is dried and the solvent evaporated.

The crude oil is at once treated at 0° C. in an ether-hexane (10–100 v/v) mixture containing 5 drops of pyridine; 15 ml of PBr$_3$ are then added to the solution. Stirring is continued for 2 h; the reaction mixture is poured into ice water and extracted with diethyl ether; the organic phase is washed with a saturated solution of NaHCO$_3$, then dried over sodium sulfate. After evaporation of the solvent, 0.31 mole of triphenyl phosphine is added to the residual oil dissolved in 200 ml of xylene and it is brought to 100° C. for 48 hours. The 1-(4-isopropyl phenyl) ethyl triphenyl phosphonium bromide is suction filtered after cooling (Yield: 76%).

(b) Preparation of (E) ethyl 4-[2-(4-isopropyl phenyl) benzoate

A mixture of 0.118 mole of 1-(4-isopropyl phenyl) ethyl bromide, 0.129 mole of p.ethoxycarbonyl benzaldehyde and 500 ml of 1,2-epoxy butane are refluxed for 12 hours. The precipitate formed is suction filtered after cooling. The solvent is evaporated from the filtrate under vacuum. The residual oil is triturated in a diethyl ether-petroleum ether (200–600 v/v) mixture. The insoluble fraction is removed by filtration. The filtrate after evaporation is crystallized in 50 ml of cold methanol.

Yield: 41%.

White crystals M.P.=65°–67° C.

NMR (CDCl$_3$): 1.26 ppm 6H (d); 1.36 ppm 3H (E); 2.26 ppm 3H (d); 2.93 ppm 1H (m); 4.40 ppm 2H (q); 6.90 1H (s.widened); 7.20 at 8.20 ppm 8H (m).

EXAMPLE 2

Preparation of (E)-4-[2-(4-isopropyl phenyl) propenyl]benzoic acid

A mixture of 0.04 mole of (E) ethyl 4-[2-(4-isopropropyl-phenyl) propenyl] benzoate, 0.1 mole of potassium, 200 ml of ethanol and 60 ml of distilled water are refluxed for 3 hours. After cooling, the reaction mixture is acidified with hydrochloric acid. The crude acid is separated by filtration, the recrystallized in methanol.

Yield: 90%.

White crystals M.P.=235°–240° C.

NMR (CDCl$_3$)+ε DMSO): 1.25 ppm 6H (d); 2.30 ppm 3H (s.widened); 2.86 ppm 1H (m); 6.90 ppm 1H (s.widened); 7.16 at 8.16 ppm 8H (m).

EXAMPLE 3

Preparation of (E)-4-[2-(4-isopropyl phenyl) propenyl]N-benzoyl morpholine (a) Preparation of (E)-4-[2-(4-isopropyl phenyl) propenyl] benzoic acid chloride 0.01 mole of the corresponding acid in the presence of 0.02 mole of thionyl chloride, 100 ml of diethyl ether, 1 ml of pyridine and 3 drops of dimethylformamide are stirred at room temperature for 20 hours. After filtration, the ether solution is evaporated and the residue triturated in benzene. After evaporation under vacuum of the benzene, the acid chloride is isolated and used in the following procedure without further purification.

Yield: 84%.

(b) Preparation of (E)-4-[2-(4-isopropyl phenyl) propenyl] N-benzoyl morpholine

Drop by drop to a solution of 0.01 mole of morpholine in 20 ml of benzene maintained under reflux, are added 0.05 mole of (E)-4-[2-(4-isopropyl phenyl) propenyl] benzoic acid chloride in 10 ml of benzene. After 4 hours under reflux, the insoluble fraction is separated by filtration, the benzene solution is evaporated under vaccum and the residue recrystallized in a diethyl ether-petroleum ether mixture.

Yield: 57%.

White crystals—M.P.: 100°-102° C.

NMR (CDCl$_3$): 1.28 ppm 6H (d); 2.28 ppm 3H (d); 2.95 ppm 1H (m); 3.72 ppm 8 H (s.widened); 6.85 ppm 1H (s.widened); 7.20 at 7.60 ppm 8H (m).

EXAMPLE 4

Preparation of N,N-diethylamino ethyl ester of (E)-4-[2-(4-isopropyl phenyl) propenyl] benzoic acid hydro-chloride 0.003 mole of (E)-4-(2-(4-isopropyl phenyl) propenyl] benzoic acid chloride in 20 ml of benzene are added dropwise to a solution of 0.006 mole of N,N-diethylaminoethanol in 30 ml of benzene. After 3 hours reflux, the benzene solution is filtered, washed with water, then dried. The solvent is evaporated under vacuum and the residual crude ester dissolved in ethyl ether is converted into the hydrochloride by bubbling gaseous hydrochloric acid through it. The hydrochloride of the ester is then recrystallized in a methanol-diethylether mixture.

Yield: 70%.

White crystals M.P.: 170°-172° C.

TABLE I

Compounds of formula I

| Compound No. | Ar | R$_1$ | R$_2$ | Yield (%) | M.P. (°C.) | Solvent of Crystallization |
|---|---|---|---|---|---|---|
| 1 |  | CH$_3$ | —OH | 75 | 195-7 | Ethanol |
| 2 | " | CH$_3$ | —O—CH$_3$ | 40 | 65-7 | Methanol |
| 3 | 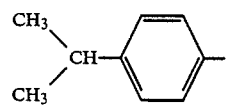 | CH$_3$ | —OH | 90 | 235-40 | Methanol |
| 4 | " | CH$_3$ | —NH$_2$ | 84 | 204-6 | Ethanol |
| 5 | " | CH$_3$ | 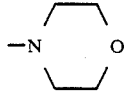 | 57 | 100-2 | Diethyl ether - Petroleum ether |
| 6 | 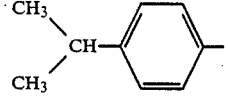 | CH$_3$ | —O—CH$_2$—CH$_3$ | 41 | 65-7 | Methanol |
| 7 | " | CH$_3$ | 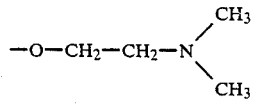 | 44 | Hydrochloride 183-5 | Methanol |
| 8 | " | CH$_3$ | 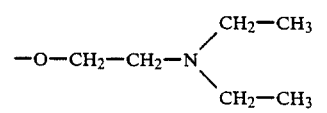 | 70 | Hydrochloride 170-2 | Methanol |
| 9 |  | CH$_3$ | —OH | 90 | 169-71 | Ethanol |
| 10 | " | CH$_3$ | —O—CH$_2$—CH$_3$ | 51 | 49-51 | Methanol |

TABLE I-continued

Compounds of formula I

| Compound No. | Ar | R₁ | R₂ | Yield (%) | M.P. (°C.) | Solvent of Crystallization |
|---|---|---|---|---|---|---|
| 11 | 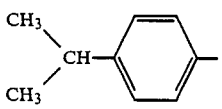 | CH₃ | 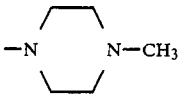 −N⌒N−CH₃ | 65 | Hydrochloride 247–249 | Methanol |
| 12 | 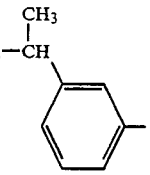 | CH₃ | −OH | 42 | 128–130 | Ethanol |
| 13 | 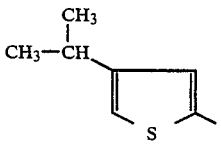 | CH₃ | −OH | 70 | 190–2 | Ethanol |
| 14 | 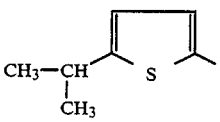 | CH₃ | −OH | 40 | 146–8 | Ethanol |

The results of pharmacological investigations demonstrating the properties of the compounds of formula I are given below.

Affinity for the cytosolic receptor of retinoic acid (C.R.A.B.P.) of rat testicles The affinity of the compounds of the formula I for the C.R.A.B.P. receptor is determined by measurement of the inhibition of the specific linking of tritiated retinoic acid (*AR) by the various compounds according to the method of ONG and CHYTIL (J. Biol. Chem., 1975, 250, 6113) modified:

The rat testicles thawed to 4° C. are placed in Tris-HCl 50 mM, DTE 2 mM buffer, pH 7.4, then ground in a Potter Teflon/glass grinder (three times at 800 rpm). The ground product is centrifuged at 4000×g for 10 min at 4° C.

The supernatant liquor is then centrifuged for 60 min at 105000×g at 4° C. to obtain the cytosol. The final protein concentration of the cytosol is adjusted to 2 mg/ml.

200 μl of cytosol are incubated for 16 h at 4° C. in the presence of tritiated retinoic acid 20 nM (specific activity: 30 Ci/mmole), in the presence of the ligands to be tested at the concentration of 4 μM.

The incubations are followed by treatment with charcoal-dextran (1%–0.0025%) for 30 min at 4° C. The bound radioactivity is determined by counting in liquid scintillation.

Table II below reports the percentages of inhibition of coupling of the tritiated retinoic acid for the compounds of the formula I possessing a —COOH group (R₂=OH), the inhibition of the linking with unmarked retinoic acid corresponding to 100% inhibition. This table establishes the affinity of these compounds for the C.R.A.B.P. receptor.

The compounds of the formula I which do not possess a free acid group do not link or little with the C.R.A.B.P. receptor and are hence not or were only weakly active in this test, but have however a similar pharmacologic activity, since they constitute apparently precursors (pro-drugs) of the compounds with an acid group.

TABLE II

| Compound No. | % Inhibition of linking with the C.R.A.B.P. receptor |
|---|---|
| Retinoic acid | 100 |
| 1 | 18.9 |
| 3 | 68.5 |
| 9 | 18.5 |
| 11 | 27.5 |
| 12 | 67.5 |
| 13 | 72.5 |
| 14 | 75.0 |

The therapeutic compositions according to the invention may be administered to man or to animals topically, orally or parenterally.

They may be in the form of solid, semi-solid or liquid preparations. As an example, may be mentioned tablets, capsules, suppositories, injectable solutions or suspensions, ointments, oily or aqueous collyria, nasal or otological solutions, colutories, as well as delayed action forms and slow-release implant forms.

In these compositions, the active ingredient generally mixed with one or several of the usual pharmaceutically acceptable carriers well known to the man skilled in the art.

The therapeutic compositions administrable topically may contain particularly from 0.001 to 5% by weight of active ingredient.

The amount of active ingredient administered depends evidently on the patient who is treated, the administrative route and the severity of the illness.

We claim:
1. Compounds of the formula

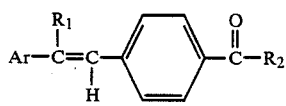

in which:

$R_1$ represents a methyl group;

Ar represents phenyl, 4-($C_{1-4}$ alkyl) phenyl, thienyl and $C_{1-4}$ alkyl thienyl;

$R_2$ represents a hydroxy group; an amino group of the formula

in which $R_3$ and $R_4$ represent, independently from one another, a hydrogen atom, a $C_1$-$C_6$ alkyl group or amino ($C_1$-$C_6$) alkyl or $R_3$ and $R_4$ form, with the nitrogen atom to which they are attached, a 5-8 membered heterocyclic group saturated or not and which can contain another heteroatom selected from nitrogen, oxygen and sulfur; $C_1$-$C_4$ alkoxy group; a group of the formula —O— Ar, Ar having the above-given meaning; and aminoalkoxy group of the formula

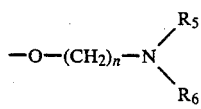

in which $R_5$ and $R_6$ represent, independently from one another a $C_1$-$C_4$ alkyl group and n=1 to 4; and their pharmaceutically acceptable salts.

2. Compounds according to claim 1, having the E configuration.

3. Compounds according to claim 2 wherein $R_2$ is an OH group.

4. Compounds according to claim 1, wherein Ar is 4-($C_{1-4}$ alkyl) phenyl and $R_2$ is selected from the group consisting of moropholino and methyl piperazino.

5. Compounds according to claim 1, wherein Ar is 4-($C_{1-4}$ alkyl) phenyl, $R_2$ is O—$(CH_2)_n$—$NR_5R_6$, and $R_5$ and $R_6$ are $C_1$-$C_4$ alkyl.

6. A stilbene compound represented by the formula (I):

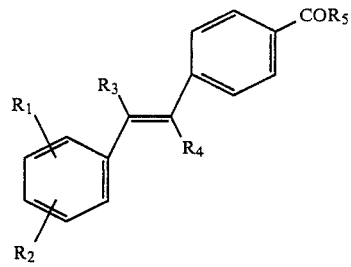

wherein $R_1$ and $R_2$ each independently represents hydrogen or lower alkyl, with the proviso that both $R_1$ and $R_2$ cannot be hydrogen simultaneously, $R_3$ and $R_4$ independently represent hydrogen or methyl, and $R_5$ represents hydroxyl, lower alkoxyl, or lower alkylamino of the formula —$NR_6R_7$, wherein $R_6$ and $R_7$ each independently represents hydrogen or lower alkyl.

7. (E)-4-[2-(2-isopropyl-5-thienyl)propenyl] benzoic acid and pharmaceutically acceptable salts thereof.

8. Therapeutic composition which comprises as active ingredient a compound according to claim 2.

9. Therapeutic composition which comprises as active ingredient a compound according to claim 3.

10. Therapeutic composition which comprises as active ingredient a compound according to claims 1.

11. Composition according to claim 10, in a topically administrable form.

12. Use of one or more stilbene derivatives of claim 6 as medicaments for treatment of dermatological disorders of humans and animals.

13. A differentiation-inducing agent for neoplastic cells, especially leukemia cells, comprising as active ingredient one or more stilbene compounds of claim 6.

14. A therapeutic agent for the treatment of cancer containing an effective amount of one or more stilbene compounds of claim 6 in a pharmaceutically acceptable carrier.

* * * * *

UNITED STATES PATENT AND TRADEMARK OFFICE
CERTIFICATE OF CORRECTION

PATENT NO. : 4,929,635

DATED : May 29, 1990

INVENTOR(S) : Claude COQUELET et al.

It is certified that error appears in the above-identified patent and that said Letters Patent is hereby corrected as shown below:

Title page item:

[73] Assignee:   Laboratoires Chauvin[-Blache]

Signed and Sealed this

Twenty-seventh Day of October, 1992

Attest:

DOUGLAS B. COMER

*Attesting Officer*       *Acting Commissioner of Patents and Trademarks*